United States Patent
Simmons

(10) Patent No.: US 11,910,863 B2
(45) Date of Patent: Feb. 27, 2024

(54) AIR PURIFICATION COOLING AND WARMING MASK

(71) Applicant: Brenda Simmons, Carmel by the Sea, CA (US)

(72) Inventor: Brenda Simmons, Carmel by the Sea, CA (US)

( * ) Notice: Subject to any disclaimer, the term of this patent is extended or adjusted under 35 U.S.C. 154(b) by 358 days.

(21) Appl. No.: 17/228,694

(22) Filed: Apr. 12, 2021

(65) Prior Publication Data
US 2021/0228003 A1     Jul. 29, 2021

Related U.S. Application Data

(62) Division of application No. 16/744,173, filed on Jan. 15, 2020, now Pat. No. 11,800,941.

(51) Int. Cl.
*A62B 23/02*     (2006.01)
*A42B 3/28*     (2006.01)

(52) U.S. Cl.
CPC ............ *A42B 3/285* (2013.01); *A62B 23/025* (2013.01); *A42B 3/286* (2013.01)

(58) Field of Classification Search
CPC .. A41D 13/11; A41D 13/005; A41D 13/0051; A41D 13/0053; A62B 23/025
See application file for complete search history.

(56) References Cited

U.S. PATENT DOCUMENTS

| | | | | |
|---|---|---|---|---|
| 3,425,486 A | * | 2/1969 | Rodney ................. | B64D 10/00 165/DIG. 46 |
| 5,291,750 A | * | 3/1994 | Parrish ................. | A41D 13/005 62/480 |
| 5,320,164 A | * | 6/1994 | Szczesuil ............. | A41D 13/005 165/46 |
| 6,105,382 A | * | 8/2000 | Reason ................ | A41D 13/005 165/46 |
| 6,109,338 A | * | 8/2000 | Butzer ................. | A41D 13/005 607/104 |
| 6,565,699 B1 | * | 5/2003 | Szczesuil ............ | B29C 66/1122 156/290 |
| 6,942,015 B1 | * | 9/2005 | Jenkins ................. | A42B 3/285 2/458 |
| 6,957,697 B2 | * | 10/2005 | Chambers ............... | F28F 21/00 165/46 |
| 7,089,995 B2 | * | 8/2006 | Koscheyev ............... | A61F 7/02 607/104 |
| 7,681,249 B2 | * | 3/2010 | Oliver .................... | B64D 10/00 2/102 |

(Continued)

FOREIGN PATENT DOCUMENTS

GB     2274239 A   *   7/1994  ........... A41D 13/005

*Primary Examiner* — Alissa L Hoey

(57) ABSTRACT

A mask which will provide air purification along with cooling and warming of a wearer's face and mouth, utilizing tubing that is filled with liquid that is detachable to the mask. The liquid is temperature controlled utilizing a thermostat and distributed by a pump. The mask is provided with removable filters, the filters clean incoming air and have filaments of organic herbs that are breathable and can serve medicinal purposes. A fan is attached to the mask to provide air circulation from outside the mask that is filtered before it reaches inside the mask to help purify the incoming air. An exhaust valve filter is placed inside the mask that filters air exiting the mask to the outside environment.

1 Claim, 1 Drawing Sheet

(56) References Cited

U.S. PATENT DOCUMENTS

| | | | | |
|---|---|---|---|---|
| 7,823,625 B2* | 11/2010 | Gammons | ............ | F16L 37/0841 |
| | | | | 165/46 |
| 8,397,517 B2* | 3/2013 | Monk | .................. | A41D 13/005 |
| | | | | 62/3.5 |
| 10,721,977 B2* | 7/2020 | Gueritee | .............. | H05B 1/0272 |
| 10,952,812 B1* | 3/2021 | Saadat | .................. | A61B 90/40 |
| 10,980,292 B2* | 4/2021 | Fan | ............................ | A61F 7/02 |
| 11,047,626 B2* | 6/2021 | Saavedra | ................ | F24T 10/10 |
| 11,247,115 B2* | 2/2022 | Blecher | ................. | A42B 3/225 |
| 11,330,852 B2* | 5/2022 | Luo | .......................... | F24F 5/001 |
| 11,358,010 B1* | 6/2022 | Rusin | ..................... | A41D 13/11 |
| 11,465,001 B2* | 10/2022 | Connor | ................. | B01D 46/46 |
| 2002/0153126 A1* | 10/2002 | Clemente | ............. | F25B 27/00 |
| | | | | 607/104 |
| 2008/0268765 A1* | 10/2008 | Luvera | ............... | A41D 13/0051 |
| | | | | 454/230 |
| 2010/0084125 A1* | 4/2010 | Goldstein | .............. | F17C 11/00 |
| | | | | 62/3.5 |
| 2010/0107657 A1* | 5/2010 | Vistakula | ........... | A41D 13/0056 |
| | | | | 62/3.5 |
| 2010/0281883 A1* | 11/2010 | Romano | ............. | A41D 13/005 |
| | | | | 62/3.5 |
| 2012/0227432 A1* | 9/2012 | Creech | ............... | A41D 13/0053 |
| | | | | 62/259.3 |
| 2013/0019611 A1* | 1/2013 | Sims | .................... | A41D 13/005 |
| | | | | 165/41 |
| 2014/0201891 A1* | 7/2014 | Turner | ................. | A41D 13/015 |
| | | | | 2/455 |
| 2014/0222121 A1* | 8/2014 | Spence | ..................... | A61F 7/02 |
| | | | | 607/104 |
| 2015/0075185 A1* | 3/2015 | Sims | ........................ | F25B 21/04 |
| | | | | 62/3.5 |
| 2015/0237927 A1* | 8/2015 | Nelson | ................. | A41D 13/005 |
| | | | | 5/413 R |
| 2016/0206018 A1* | 7/2016 | Barbret | .............. | A41D 13/0053 |
| 2018/0014585 A1* | 1/2018 | Polonio | .................. | A41D 27/00 |
| 2019/0009114 A1* | 1/2019 | Han | ....................... | A41D 1/002 |
| 2019/0104774 A1* | 4/2019 | Paiva | ......................... | A61F 7/02 |
| 2020/0329788 A1* | 10/2020 | Su | ....................... | A41D 13/0053 |
| 2021/0037900 A1* | 2/2021 | Itao | ......................... | A61F 7/007 |
| 2021/0106459 A1* | 4/2021 | Caruso | .................... | G06F 3/011 |
| 2021/0352974 A1* | 11/2021 | Kirchmeier | .......... | A41D 13/005 |
| 2022/0072340 A1* | 3/2022 | Nitta | ........................ | A62B 7/10 |
| 2022/0266068 A1* | 8/2022 | Connor | .................... | A62B 7/10 |
| 2023/0051351 A1* | 2/2023 | Pare | .......................... | A45F 3/04 |

* cited by examiner

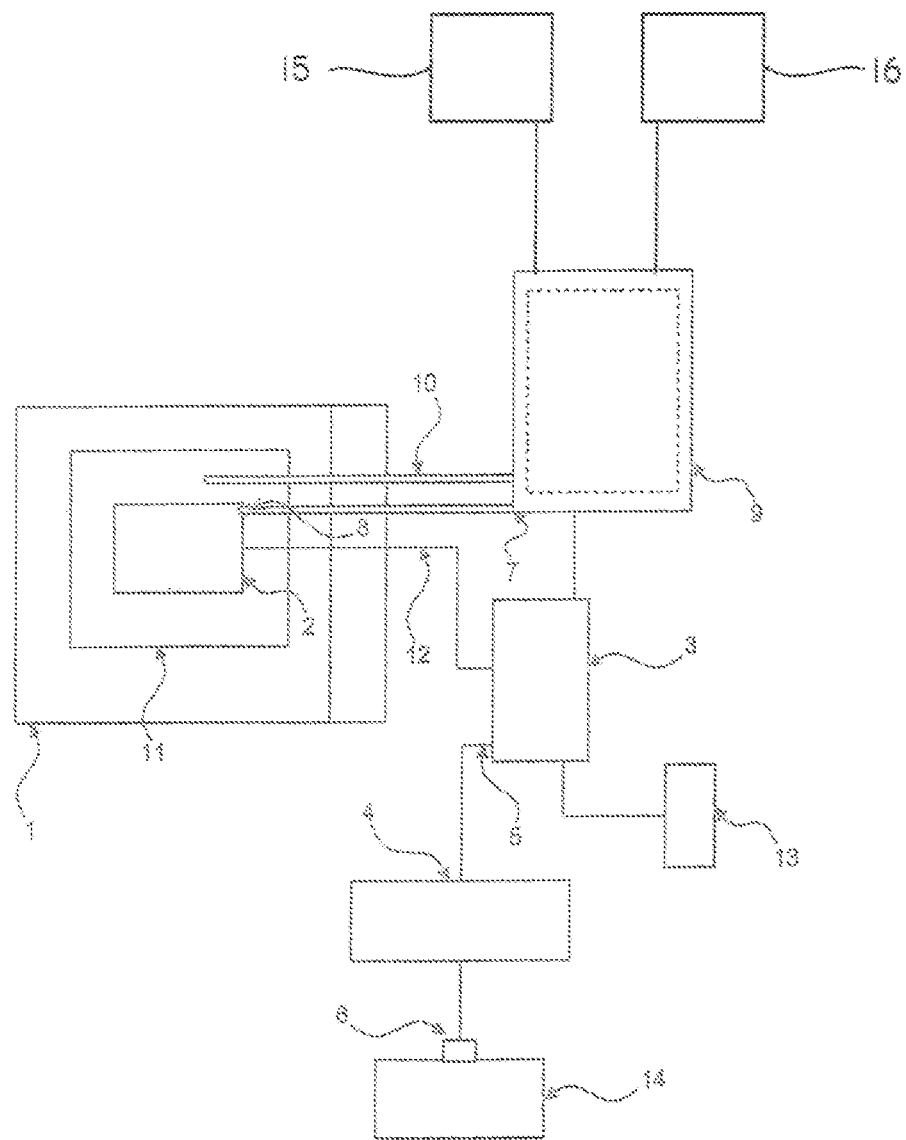

AIR PURIFICATION COOLING AND WARMING MASK

RELATED APPLICATIONS

The present application claims priority to U.S. Provisional Application No. 62/792,871 filed Jan. 15, 2019 and is a Divisional to U.S. application Ser. No. 16/744,173 filed Jan. 15, 2020, the contents which are incorporated herein in their entirety.

BACKGROUND OF THE INVENTION

The present invention is directed to an air purification mask to help prevent various kinds of viruses and bacteria contaminants from being breathed in or out of the mask body. The mask also provides cooling and warming, utilizing tubing that is filled with liquid that is detachable to the mask. The liquid is capable of cooling or warming the user and promotes health and healing for various applications to help prevent various kinds of viruses and bacteria contaminants.

BRIEF SUMMARY OF THE INVENTION

The present invention relates to an air purification mask that houses a fan to distributes air throughout the mask, the mask is embedded with detachable filters, to help purify the air and are provided with organic herbal fragrance. The filters can be chosen from HEPA, activated carbon filters, and other filters that assist with eliminating toxic contaminates. The filters are washable and reusable for several applications. Tubing is attached to the mask to control cooling and or warming through liquid to provide comfort to the user. The temperature of the liquid is controlled by user by way of a thermostat, depending on the application that is use.

BRIEF DESCRIPTION OF THE DRAWINGS

FIG. 1 is a diagrammatic representation of the mask with cooling/warming supply system.
(1) carrying bag
(2) pump
(3) thermostat
(4) regulator
(5) wires connected regulator and thermostat
(6) USB connection
(7) distal end of tubing
(8) valve connection
(9) mask
(10) tubing
(11) container
(12) pump wires
(13) probe
(14) battery
(15) fan
(16) filter

DETAILED DESCRIPTION OF THE DRAWINGS

FIG. 1 details a container (11) that is filled with liquid and a pump (2), tubing (10) is connected to an outlet on the pump (2) which pumps liquid from the container to the mask (9) for warming or cooling. A shut off valve (8) is incorporated to control liquid flow. The pump wiring (12) is connected to the thermostat (3) and the regulator (4) is connected to the battery (6) via a USB connection (6). The mask fan (15) is connected to the mask with wiring that connects to the thermostat (3). The fan (15) is attached to mask for the inflow of air through the filters (16) inside the mask.

DETAILED DESCRIPTION OF THE INVENTION

The present invention relates to a mask that provides filtration of air to and from the mask while also providing warming and/or cooling via liquid in tubing attached to the mask. A container is filled with liquid and has a pump, the tubing is connected to an outlet in the pump that transports the liquid from the container through the tubing that is attached to the mask. The filters of the mask are reusable and replaceable to provide air filtration and a fan is attached to the mask. The electronic operation is connected to the pump inside the container filled with the liquid to send it into the tubing which is embedded, attached or detachable placed within the mask. The pump is charged by battery and or solar utilizing a USB connection for outdoor activity or electricity for indoor operations. The cool temperature is created by the use of icepacks inside a carrying bag that surrounds the container therein. The liquid can also have ice cubes placed inside the container that help maintain cool temperatures that transmits to the tubing and flows inside the mask and then recirculated back to the container during operation. This enables cooling of liquid transferred to the pump to the tubing inside the mask as needed for outdoor or indoor temperature environments for comfort of the given user. The heating apparatus uses hot water or a heating pad charged by battery and/or solar. In addition, but not limited to, the ice packs can be converted to heating packs. The user can put hot liquid into the container to assist in maintaining warm liquid to the pump that is distributed to the tubing inside the mask and recirculated back through the container. This invention enables comfort to the user for warmth outside/inside in a cold environment and cooling during hot humid, dry heat inside/outside. The duration of the battery charge can last up to 10 hours or more on a single charge depending on the type of rechargeable battery used. The liquid can be cooled or warmed by numerous ways including but not limited to, cooling and/or heating cells, electronic cooling or heating apparatuses, heat wire modules, and a Peltier with voltage to the container for indoor operations. The temperature is adjusted by the thermostat to degrees and/or Celsius to cool or warm the liquid that is transmitted by the pump inside the tubing during recirculation to the mask and back to the container. The temperature controlled thermostat is connected to the auxiliary bag that houses the container with the liquid, the pump, charger, connectors, tubing outlets and the above discussed cooling and heating mediums and/or apparatuses.

A fan can be attached to the mask in several locations for air circulation that will flow through the filters that are embedded inside the mask. The filters are of high quality which will provide 99.9 or more filtration capabilities to help prevent VOC's and various bacteria viruses from the entering the mask. In addition, an exhaust valve is attached with an additional filter(s) to expel cleaner air flow outside the mask environment. The air purification face mask can be worn to protect from the Covid virus.

The cover can take the form of a mask that covers the face, undergarments, garments of all sizes, bedding, head coverings, and head to toe covers to be utilized for the humans and domestic mammals. The cooling (cold) systems and warming (heated) systems connected to the covering can be interchangeable to accommodate a variety of covering with numerous fabrics and construction materials but not limited to, colors, textures and numerous embodiments. The covers can be detachable/removed to service other covers such as garments coverings, that in some cases will require custom designs and configurations from the manufacturer with the proper measurements that suits the applications the client, customer, and user(s) needs. The cover will help in hot climates to provide cooler temperatures for relief of human and or to domestic mammal's body from head to toe. In addition, in colder climates the cover will help keep a user's body at a comfortable level.

The liquid is put into the container whether it is cold or hot, then the pump is inserted into the liquid. The pump should have suction cups or adhering materials to maintain stability to the container during movement of the user. The pump should not be operated without the liquid because it can burn out the pump operation. The tubing is connected to the pump, then the tubing emerges thru the top of the container. The tubing is elongated and attached to a turn off valve at the end, then the tubing is attached to the connection of the valve. The remainder of the elongated tubing should be measured to the appropriate length to provide a length that is embedded or attached to the surface of the mask and then the remaining tubing extends inside the container top to flow liquid back inside to recirculate the liquid via the pump. The wires to the pump extend thru the top of the container. The opening of the container is sealed to contain the liquid from coming out of it. The top of the container is sealed to contain the liquid therein. The wires from the pump are connected to the thermostat e-channels via the voltage regulator. The other end of the voltage regulator will have a USB connection. The voltage USB connection will be inserted into the battery charger input locator when ready to operate the pump and flow of liquid into the tubing. The thermostat is set to the desired temperature by the user.

The tubing is embedded or attached to the mask and can be detachable. Attachments can be used to attach to the tubing and the mask. A strip of material and/or fabric should cover the tubing to attach the tubing to the mask. The fabric of material attaching the tubing provides comfort to the skin and/or fur to the user. The cut off valve can be placed in several locations on the mask and is not limited to certain number of valves. The user or operator will prepare the liquid to cool or warm the user as desired. An additive is inserted into the liquid to keep the liquid from contamination and allows for flow durability and longevity over time. A timer can be attached or detached to the container to determine the required timing of the operations if needed, or the operations can be determined manually, or by remote control.

An auxiliary bag or container houses the container and the electronic components, and comprises a separate compartment for the battery, an area for the thermostat inside the compartment, an outside area for the probe of the thermostat to be exposed, and a compartment for phone, wallet and/or other necessities within the auxiliary bag. The bag can be carried several ways across the users body, by hand, as a back pack, on the shoulders, a strap on the body, laid across the body, and other numerous ways to facilitate the utility of the operation in the invention and alignment of the mask.

What is claimed is:

1. A portable cooling and warming mask comprising:
  a mask body configured to be worn on a wearer's face and mouth, wherein at least one filter is releasably attached to an interior of the mask body to filtrate air, wherein the at least one filter is reusable and washable, wherein the at least one filter comprises organic herbs configured to serve medicinal purposes to the wearer during breathing, wherein the mask body comprises an attachable fan configured to provide air circulation from outside the mask body, wherein an exhaust valve filter is attached to an inside of the mask body and is configured for filtrating air exiting the mask, wherein tubing is wound around and releasably attached to the mask body providing pathways for cooled or heated liquid to flow therethrough, wherein the tubing is provided with one or more valves to direct the flow of liquid throughout the mask body and to control a temperature of a portion of the mask for comfort and/or therapeutic purposes, wherein the tubing is attached to the mask body by a strip of fabric that is secured to the interior of the mask body and is configured to be a protective layer between the tubing and the face of the wearer;
  a sealable container that is configured to recirculate the liquid from the container, through container tubing, and to the tubing of the mask body, wherein the container houses a pump, wherein the pump has a bottom with suction cups, wherein the suction cups attach to the container to hold the pump in place during use, wherein the container tubing is connected to the pump within the container and extends through a top opening of the container, the container tubing emerges from the top opening and releasably attaches to the tubing of the mask body;
  a thermostat is connected to the pump with wires that extend from the pump through the top of the container and to outside channels of the thermostat, wherein the thermostat is programmable and configured to adjust a temperature of the liquid transmitted by the pump to the container tubing and to the tubing of the mask body; and
  a carrying bag having an attached carrying strap that is configured to be carried by the wearer, wherein the carrying bag comprises a first compartment which houses the container, a second separate compartment which houses the battery and the thermostat, and a third separate compartment configured to house personal necessities, wherein the carrying bag has an opening in the second compartment through which a probe of the thermostat extends to be positioned on an outside of the carrying bag.

* * * * *